(12) United States Patent
Shin

(10) Patent No.: US 11,896,984 B2
(45) Date of Patent: Feb. 13, 2024

(54) CONTAINER FOR CENTRIFUGATION

(71) Applicant: Hyun Sun Shin, Seoul (KR)

(72) Inventor: Hyun Sun Shin, Seoul (KR)

( * ) Notice: Subject to any disclaimer, the term of this patent is extended or adjusted under 35 U.S.C. 154(b) by 828 days.

(21) Appl. No.: 16/499,863

(22) PCT Filed: Mar. 30, 2018

(86) PCT No.: PCT/KR2018/003831
§ 371 (c)(1),
(2) Date: Sep. 30, 2019

(87) PCT Pub. No.: WO2018/182378
PCT Pub. Date: Oct. 4, 2018

(65) Prior Publication Data
US 2020/0023381 A1 Jan. 23, 2020

(30) Foreign Application Priority Data
Mar. 30, 2017 (KR) .................. 10-2017-0040570

(51) Int. Cl.
*B04B 7/08* (2006.01)

(52) U.S. Cl.
CPC ......... *B04B 7/08* (2013.01); *B01L 2300/0864* (2013.01); *B01L 2400/0409* (2013.01)

(58) Field of Classification Search
CPC ............... B04B 7/08; B01L 2300/0864; B01L 2400/0409; B01L 2200/0684; B01L 2200/0689; B01L 2300/042; B01L 2300/046; B01L 2300/048; B01L 2300/0832; B01L 2400/0688; B01L 3/50215; B01L 3/5021; B01L 3/00; A61M 1/3696; B01D 17/0217; G01N 33/491; G01N 2001/4083
USPC ...................................................... 494/16, 17
See application file for complete search history.

(56) References Cited

U.S. PATENT DOCUMENTS

| 5,707,331 A | 1/1998 | Wells et al. |
| 5,895,346 A | 4/1999 | Wells et al. |
| 5,899,349 A | 5/1999 | Moore |
| RE38,730 E | 4/2005 | Wells et al. |

(Continued)

FOREIGN PATENT DOCUMENTS

| CN | 106148176 A | 11/2016 |
| JP | 61090695 U | * 6/1986 |

(Continued)

*Primary Examiner* — Walter D. Griffin
*Assistant Examiner* — Shuyi S. Liu
(74) *Attorney, Agent, or Firm* — RABIN & BERDO, P.C.

(57) ABSTRACT

The present invention relates to a container for centrifugation. The container for centrifugation includes: a main body (100) including a first chamber (110) in which a material to be centrifuged is received, a second chamber (120) in which a suspended material centrifuged from the material in the first chamber (110) is decanted from the first chamber (110) and received and which is positioned on one side of the first chamber (110), and a coupling part (130) formed to surround the first chamber (110) and the outside of the upper end of the second chamber (120); and a cover (200) which covers an upper portion of the main body (100) and forms a fluid communication path (P) of the decanted suspended material between the first chamber (110) and the second chamber (120).

4 Claims, 6 Drawing Sheets

(56) References Cited

U.S. PATENT DOCUMENTS

| | | | |
|---|---|---|---|
| RE38,757 E | | 7/2005 | Wells et al. |
| 8,998,000 B2 * | | 4/2015 | Crawford ........... B01D 17/0217 |
| | | | 422/918 |
| 2005/0247715 A1 * | | 11/2005 | Ellsworth ............. B04B 5/0421 |
| | | | 220/501 |

FOREIGN PATENT DOCUMENTS

| | | | |
|---|---|---|---|
| JP | 3129670 U | * | 3/2007 |
| JP | 4395207 B2 | | 1/2010 |
| JP | 2010043876 A | | 2/2010 |
| JP | 2013240793 A | | 12/2013 |
| KR | 100435264 B1 | | 7/2004 |
| KR | 101197908 B1 | | 11/2012 |
| KR | 101197974 B1 | | 11/2012 |

* cited by examiner

CONTAINER FOR CENTRIFUGATION

TECHNICAL FIELD

The present invention relates to a container for centrifugation which is mounted in a centrifuge, and more specifically, to a container for centrifugation in which when centrifugation is performed by means of a difference in the specific gravity of respective components by applying a centrifugal force to a biological complex fluid such as blood or bone marrow, a valve body for defining a boundary layer between deposited materials and suspended materials which have been centrifuged is configured to reciprocate and be prevented from rotation, and a path through which the suspended materials separated from the deposited materials move is widely secured, thereby rapidly separating and recovering a desired component layer.

BACKGROUND ART

A centrifuge is a device for separating materials using a centrifugal force generated when an object rotates. In biotechnology, centrifuges are used for the purpose of separating materials with higher specific gravity and adhesion than cells mixed with liquid or a liquid by specific gravity. When a complex fluid such as blood is centrifuged using the centrifuge, the fluid is divided into several layers due to the difference in specific gravity.

Although blood is used as a major indicator for determining various diseases and health conditions, platelets rich in growth factors in the blood are used for therapeutic purposes. The blood consists of red blood cells, white blood cells, platelets, etc., and the platelets are mainly in the plasma, and the plasma is classified into a platelet rich plasma (PRP) layer and a platelet poor plasma (PPP) layer. Among these, since the PRP plays a role in stimulating stem cells around an implanted site to produce cells when the PRP is implanted in pain areas, especially in the knee ankle, ligament, and muscle, the PRP have been used for therapeutic purposes. However, since the content of the PRP in the blood is small and the PRP is attached to the red blood cells, it is difficult for the PRP to be extracted, and when the red blood cells enter the human body, considerable pain is caused to cause inflammation, and thus the centrifuge is used to separate the red blood cells and the plasma and extract the PRP from the plasma.

The centrifuge is classified into various types according to the amount of a sample to be centrifuged, a rotation speed, a type of rotor, etc. In the centrifuge, a plurality of chambers is included to accommodate a material to be centrifuged, separate the material into several layers according to a difference in specific gravity by the centrifugal force, and recover by decanting a part of the separated layer (pouring the suspended material into another chamber).

As the prior art of such a centrifuge, in Korean Patent Registration No. 10-0435264, the centrifuge includes a plurality of chambers for accommodating a material to be centrifuged, a means for rotating the chambers to centrifuge the material, and a means for fixing the chambers to a predetermined position so as to discharge a suspended material in a first chamber among the chambers to a second chamber, in which the a disk suspended on a boundary layer between the materials to be centrifuged is included in the first chamber and a groove is formed on one side of the disk so that the suspended material to be centrifuged may pass through the other side of the disk.

According to such a configuration, while centrifuging or after centrifuging, the sample container is fixed in a selected direction to separate and discharge the suspended material between two or more chambers of the container. However, since the disk has a structure in which a hollow tube is inserted in a central portion thereof and a groove for communicating the fluid is formed on one side of the disk, the disk moves in a longitudinal direction of the first chamber and simultaneously rotates and swings in response to a change of the boundary layer of the material to be centrifuged in the centrifuging process, and the centrifuged suspended material is smoothly moved by the interference with the groove formed on the disk, and as a result, there is a problem that a lot of time is required for the centrifugation.

Further, according to the related art, since the first chamber and the second chamber are disposed adjacent to each other in parallel and the fluid communication between the chambers is performed only through a bridge formed on a cover, a cross-sectional area of a path through which the suspended material centrifuged moves to the other chamber is formed to be small and as a result, there is a problem that it takes a lot of time to decant the suspended material.

In order to solve the problems, in a patent for a container for centrifugation as Korean Patent Registration No. 10-1197908, the present applicant proposes a container for centrifugation comprising a main body including a first chamber in which a material to be centrifuged is received and a second chamber in which suspended materials centrifuged from the material in the first chamber are received after being decanted from the first chamber and which is positioned on one side of the first chamber; and a cover which covers the top of the main body and has fluid communication path of the decanted suspended material between the first chamber and the second chamber, wherein the main body has a guide part which communicates through the path, surrounds the entire outer surface of the first chamber to induce the decanted suspended material, and is inclined toward the second chamber.

Further, in a patent for a container for centrifugation capable of rapidly centrifuging as Korean Patent Registration No. 1197974, the present applicant proposes a container for centrifugation comprising a container for centrifugation comprising a main body including a first chamber in which a material to be centrifuged is received and a second chamber in which a suspended material centrifuged from the material in the first chamber are received after being decanted from the first chamber and which is positioned on one side of the first chamber; and a cover which covers the top of the main body and has fluid communication path of the decanted suspended material between the first chamber and the second chamber, wherein the first chamber includes a valve body which is disposed to linearly reciprocate in a longitudinal direction of the first chamber and has a plurality of through-holes on the bottom surface thereof, and in the centrifuging process, the centrifuged suspended material moves through the plurality of through-holes and simultaneously moves through a gap formed between the outer surface of the valve body and the inner surface of the first chamber.

In the problems of the related arts, since an adhesive has been used when coupling the cover and the main body, it is not easy to be assembled and fabricated.

In addition, in the related arts, there is a problem in that an inlet port and a discharge port are merely formed of a rubber material to make it difficult to inflow or discharge an injection needle through a correct position.

Further, in the related arts, since the valve body is in contact with the bottom of the first chamber, the material to be centrifuged is fully introduced to the top of the valve body, so that buoyancy can not be easily applied, and as a result, there have been some limitations in separating the suspended material depending on specific gravity.

DISCLOSURE

Technical Problem

The present invention is contrived to solve the above problems, and an object of the present invention is to provide a container for centrifugation capable of accurately performing separation of ingredient materials by separating ingredient materials constituting a biological complex fluid such as blood or bone marrow using a centrifugal force by rotation of the centrifuge and a difference in specific gravity for each ingredient.

Another object of the present invention is to provide a container for centrifugation with high operation efficiency capable of easily assembling a cover and a main body.

Yet another object of the present invention is to provide a container for centrifugation having an inlet port and a discharge port capable of easily introducing a material to be centrifuged and discharging a suspended material through the inlet port and the discharge port.

Technical Solution

An aspect of the present invention provides a container for centrifugation comprising: a main body 100 including a first chamber 110 in which a material to be centrifuged is received, a second chamber 120 in which a suspended material centrifuged from the material in the first chamber 110 is decanted from the first chamber 110 and received and which is positioned on one side of the first chamber 110, and a coupling part 130 formed to surround the first chamber 110 and the outside of the upper end of the second chamber 120; and a cover 200 which covers an upper portion of the main body 100 and forms a fluid communication path P of the decanted suspended material between the first chamber 110 and the second chamber 120, wherein the inside of the first chamber 110 has valve bodies 140, 140', 140", and 140''' which are disposed to linearly reciprocate in a longitudinal direction of the first chamber 110 to be positioned on a boundary layer between the centrifuged materials and have through-holes 145, 145', 145", and 145''' formed on the bottom surface and through which the material to be centrifuged is separately moved, the cover 200 is configured by a ring part 230 which forms the rim of the cover 200 and is formed to be coupled to the coupling part 130 at the rim of the cover, a recess part 220 which is connected to the inner side of the ring part 230 to be formed in a recessed shape, and a protrusion part 210 which is connected to the inner side of the recess part 220 and formed in a protruding shape to form the fluid communication path P so that the suspended material is discharged from the first chamber 110 to the second chamber 120, in the protrusion part 210, an inlet port 212 is formed to protrude from the protrusion part 210 for injecting the material to be centrifuged to the first chamber 110, the recess part 220 has an air vent for discharging inner air by injecting the material to be centrifuged to the first chamber 110 and a discharge port for discharging a suspended material introduced into the second chamber 120, the ring part 230 includes an outer ring part 231, a planar ring part 232 connected to the outer ring part 231, and an inner ring part 233 which is connected with the planar ring part 232 and has a stepped portion, wherein a ring hook 231-1 is formed on an inner peripheral surface of the outer ring part 231, and an outer end portion of the coupling part 130 has a coupling hook 131 which is extended upward and corresponds to an outer peripheral surface so as to be coupled with the ring hook 231-1 of the outer ring part 231.

In the present invention, the valve body 140 may be configured by an inner bottom surface 143, an outer bottom surface 141 forming a lower surface of the inner bottom surface 143, an inner surface 144 connected with the inner bottom surface 143, an outer surface 142 forming the outer portion of the inner surface 144 and connected with the outer bottom surface 141, and a through-hole 145 formed by passing through the inner bottom surface 143 and the outer bottom surface 141 to be formed in a cup shape as a whole, and a foot plate 141-1 may protrude from the outer bottom surface 141 and the inner surface 144 may have a first slope surface 144-1 and a second slope surface 144-2 formed sequentially from the lower portion to the upper portion for smooth movement of the suspended material.

In the present invention, the valve body 140' may be configured by an inner bottom surface 143', an outer bottom surface 141' forming a lower surface of the inner bottom surface 143', an inner surface 144' connected with the inner bottom surface 143', an outer surface 142' forming the outer portion of the inner surface 144' and connected with the outer bottom surface 141', and a through-hole 145' formed by passing through the inner bottom surface 143' and the outer bottom surface 141' to be formed in a cup shape as a whole, and a foot plate 141-1' protrudes from the outer bottom surface 141', the inner surface 144' has a first slope surface 144-1' and a second slope surface 144-2' formed sequentially from the lower portion to the upper portion for smooth movement of the suspended material, the outer surface 142' has a larger diameter upward and is formed so as to be inclined upward, and the upper end of the outer surface 142' has an outer surface minute protrusion part 142-1' minutely protruding outward along the outer peripheral surface.

In the present invention, the valve body 140" may be configured by an inner bottom surface 143", an outer bottom surface 141" forming a lower surface of the inner bottom surface 143", an inner surface 144" connected with the inner bottom surface 143", an outer surface 142" forming the outer portion of the inner surface 144" and connected with the outer bottom surface 141", and a through-hole 145" formed by passing through the inner bottom surface 143" and the outer bottom surface 141" to be formed in a cup shape as a whole, and a foot plate 141-1" may be formed to protrude from the outer bottom surface 141", the inner surface 144" may form a gentle slope surface 144-1" at a predetermined angle from the lower portion to the upper portion for smooth movement of the suspended material, and the end portion of the inner surface may have a cutting surface 144-2" cut along the inner peripheral surface to reduce the load.

In the present invention, the valve body 140''' may be configured by an inner bottom surface 143''', an outer bottom surface 141''' forming a lower surface of the inner bottom surface 143''', an inner surface 144''' connected with the inner bottom surface 143''', an outer surface 142''' forming the outer portion of the inner surface 144''' and connected with the outer bottom surface 141''', and a through-hole 145''' formed by passing through the inner bottom surface 143''' and the outer bottom surface 141''' to be formed in a cup shape as a whole, and a foot plate 141-1''' may be formed to protrude from the outer bottom surface 141''', the inner surface 144''' may form a slope surface 144-1''' at a predetermined angle to the upper portion from the lower portion for smooth movement of the suspended material, the outer surface 142''' may have a larger diameter toward the upper portion so that the cross section has a shape inclined outward, and the upper end of the outer surface 142''' may have an outer surface minute protrusion part 142-1''' protruding outward along the outer peripheral surface.

In the present invention, a packing ring 300 in inserted into a space formed by the coupling part 130 and a stepped portion of the inner ring part 233.

In the present invention, injection needle guides 212-1 and 222-1 having holes 212-1(1) and 222-1(1) formed in the center may be coupled to the inlet port 212 and the upper end of the discharge port 222.

In the present invention, the through-holes 145 and 145' may be configured by straight pipe parts 145-1 and 145-1' formed upward from the outer bottom surfaces 141 and 141' and enlarged pipe parts 145-2 and 145-2' of which diameters are enlarged to the upper portion from the end portion of the straight pipe parts 145-1 and 145-1', and in order to extend the enlarged pipe parts 145-2 and 145-2', the inner bottom surfaces 143 and 143' may be provided with hill parts 143-1 and 143-1' protruding from the center thereof.

In the present invention, the through-holes 145" and 145''' may be configured by undercut parts 145-3" and 145-3''' formed for smooth flow of the suspended material upward from the outer bottom surfaces 141" and 141''', straight pipe parts 145-1" and 145-1''' formed on the upper portion of the undercut parts 145-3" and 145-3''', and enlarged pipe parts 145-2" and 145-2''' of which diameters are enlarged to the upper portion from the end portion of the straight pipe parts 145-1" and 145-1''', and in order to extend the enlarged pipe parts 145-2" and 145-2''', the inner bottom surfaces 143" and 143''' may be provided with hill parts 143-1" and 143-1''' protruding from the center thereof.

Advantageous Effects

According to the exemplary embodiments of the present invention, it is possible to rapidly and accurately separate ingredient materials constituting a biological complex fluid such as blood or bone marrow by a centrifugal force by rotation of the centrifuge.

In addition, since the assembling is performed only by inserting the cover and the main body, the workability is improved and the work efficiency may be improved.

In addition, an injection needle guide for accurately injecting the injection needle into the inlet port and the discharge port is formed, thereby facilitating the introduction of the complex fluid such as blood or bone marrow and the discharge of the separated suspended material.

In addition, since an area of the valve body contacting the inner wall of the first chamber is small, the operation by buoyancy may be performed quickly.

MODES OF THE INVENTION

Figure 1:
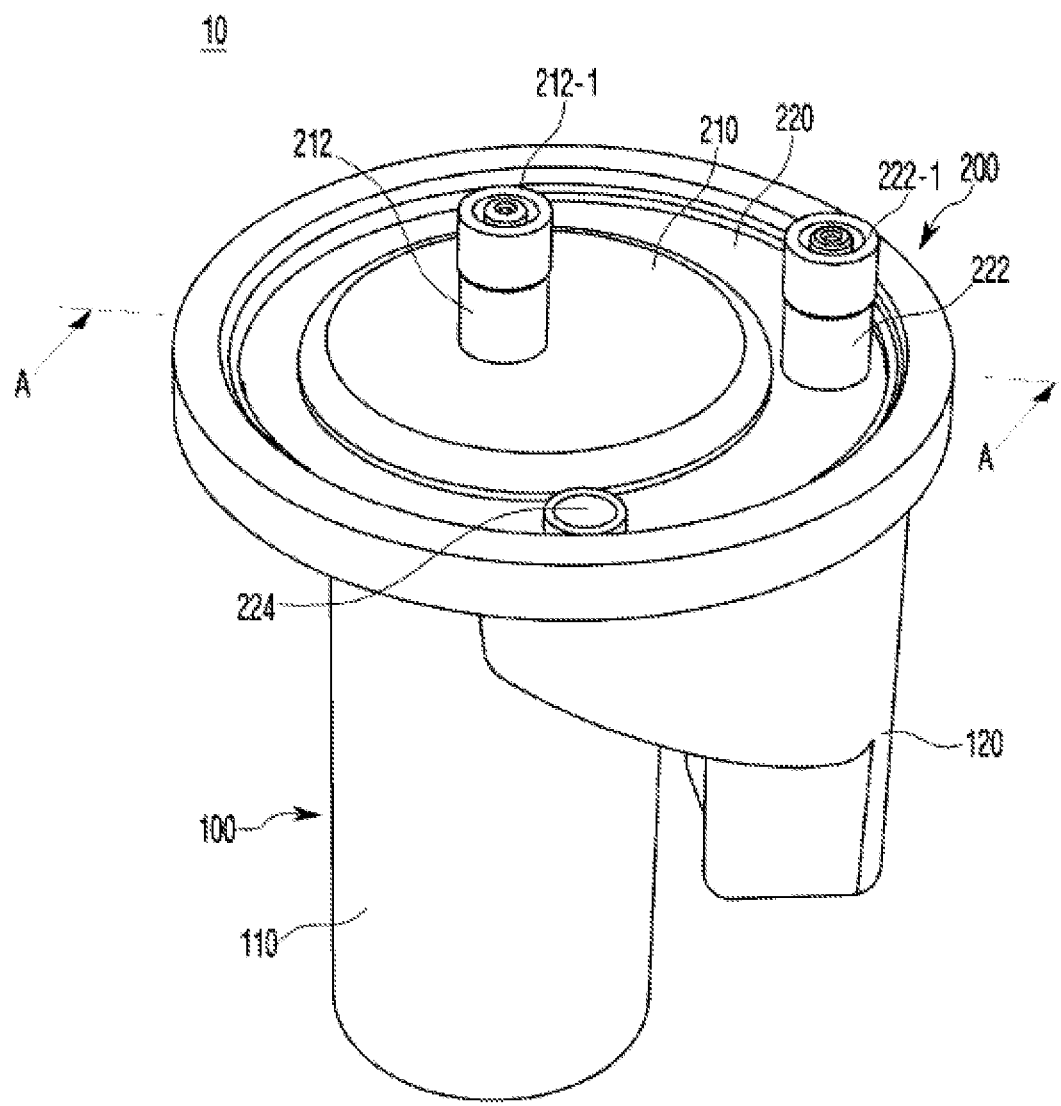
FIG. 1 is a perspective view of a container for centrifugation according to an exemplary embodiment of the present invention.

A best aspect of the present invention provides a container for centrifugation comprising: a main body 100 including a first chamber 110 in which a material to be centrifuged is received, a second chamber 120 in which a suspended material centrifuged from the material in the first chamber 110 is decanted from the first chamber 110 and received and which is positioned on one side of the first chamber 110, and a coupling part 130 formed to surround the first chamber 110 and the outside of the upper end of the second chamber 120; and a cover 200 which covers an upper portion of the main body 100 and forms a fluid communication path P of the decanted suspended material between the first chamber 110 and the second chamber 120, wherein the inside of the first chamber 110 has valve bodies 140, 140', 140", and 140''' which are disposed to linearly reciprocate in a longitudinal direction of the first chamber 110 to be positioned on a boundary layer between the centrifuged materials and have through-holes 145, 145', 145", and 145''' formed on the bottom surface and through which the material to be centrifuged is separately moved, the cover 200 is configured by a ring part 230 which forms the rim of the cover 200 and is formed to be coupled to the coupling part 130 at the rim of the cover, a recess part 220 which is connected to the inner side of the ring part 230 to be formed in a recessed shape, and a protrusion part 210 which is connected to the inner side of the recess part 220 and formed in a protruding shape to form a fluid communication path P so that the suspended material is discharged from the first chamber 110 to the second chamber 120, in the protrusion part 210, an inlet port 212 is formed to protrude from the protrusion part 210 for injecting the material to be centrifuged to the first chamber 110, the recess part 220 has an air vent for discharging inner air by injecting the material to be centrifuged to the first chamber 110 and a discharge port for discharging a suspended material introduced into the second chamber 120, the ring part 230 includes an outer ring part 231, a planar ring part 232 connected to the outer ring part 231, and an inner ring part 233 which is connected with the planar ring part 232 and has a stepped portion, wherein a ring hook 231-1 is formed on an inner peripheral surface of the outer ring part 231, and an outer end portion of the coupling part 130 has a coupling hook 131 which is extended upward and corresponds to an outer peripheral surface so as to be coupled with the ring hook 231-1 of the inner ring part 231.

Hereinafter, configurations and functions of preferred exemplary embodiments of the present invention will be described in detail with reference to the accompanying drawings.

Figure 2:
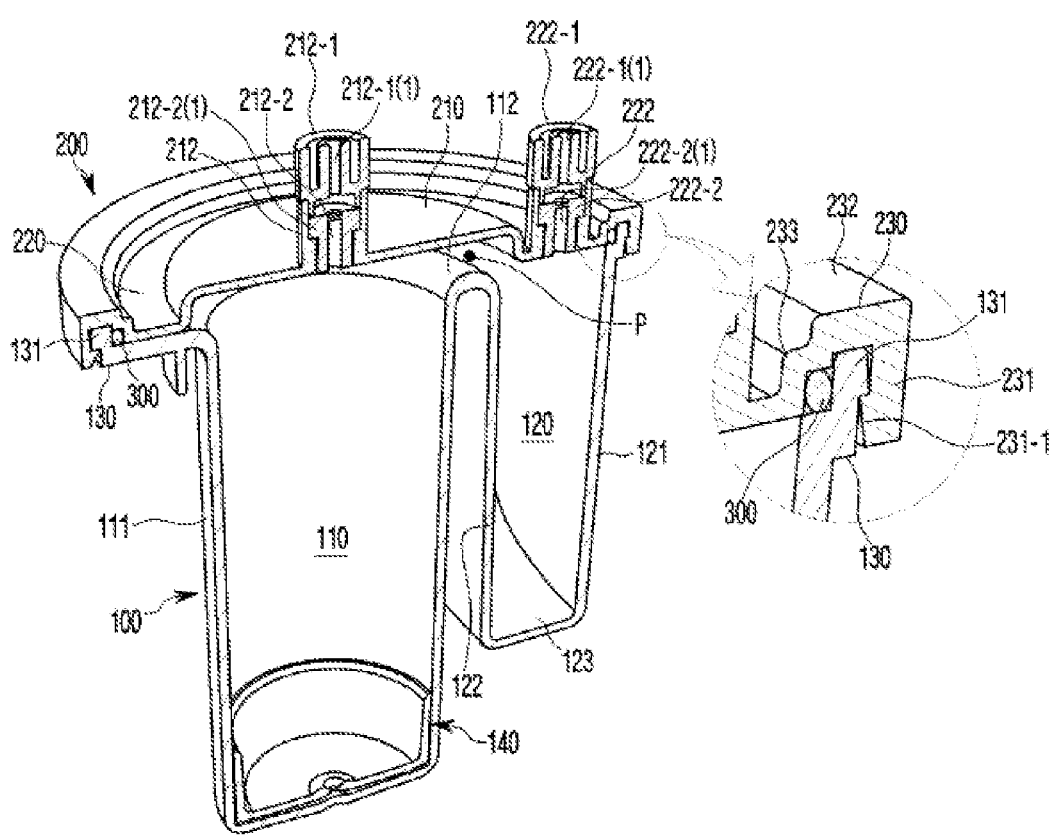
FIG. 2 is a perspective view of a cross section A-A of FIG. 1.
Figure 3:
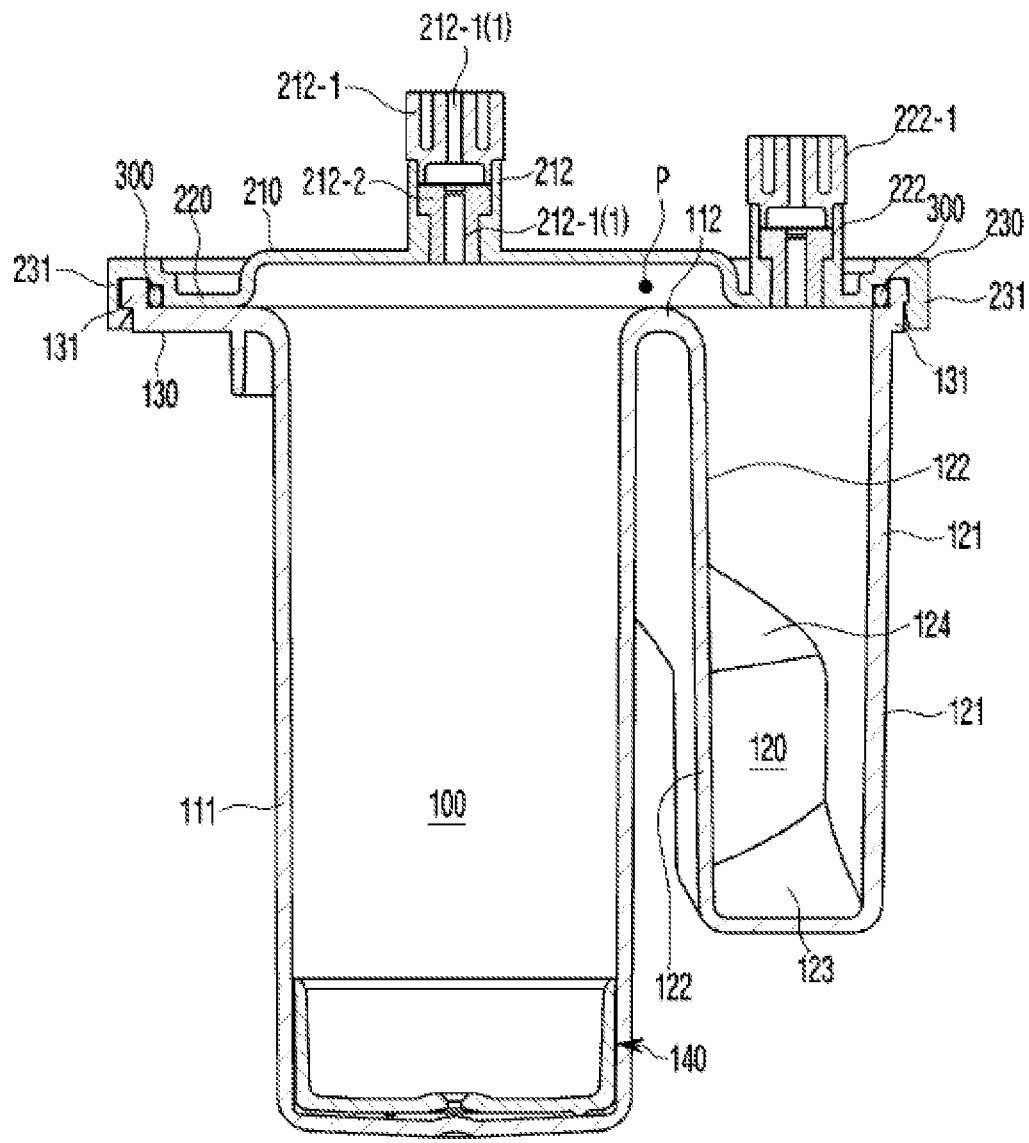
FIG. 3 is a cross-sectional view of A-A of FIG. 1.
Figure 4:
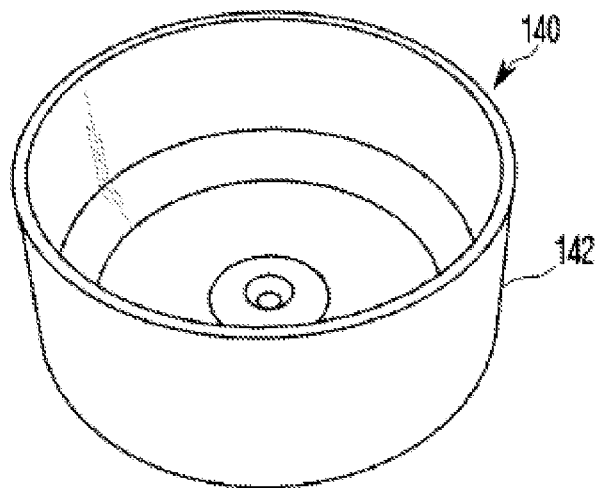
FIG. 4 is a perspective view of a first embodiment of a valve body according to the present invention.
Figure 5:
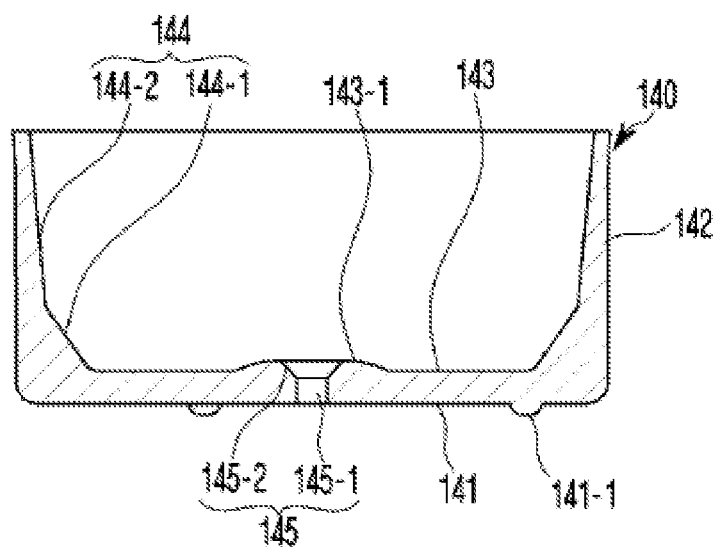
FIG. 5 is a cross-sectional view of the valve body of FIG. 4.
Figure 6:
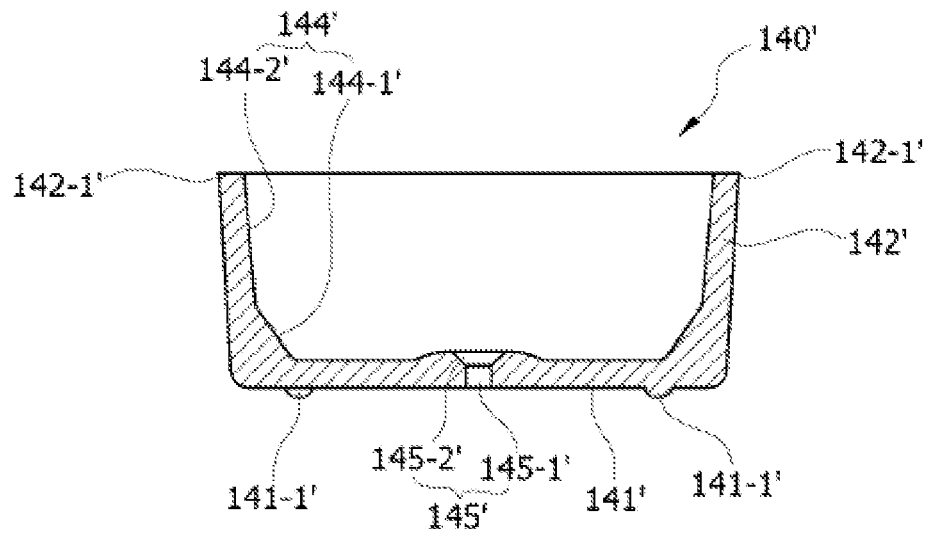
FIG. 6 is a cross-sectional view of a second embodiment of the valve body according to the present invention.
Figure 7:
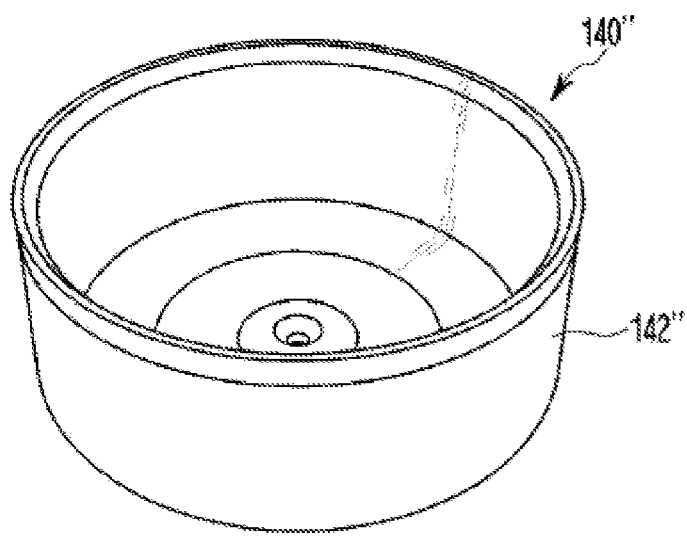
FIG. 7 is a perspective view of a third embodiment of the valve body according to the present invention.
Figure 8:
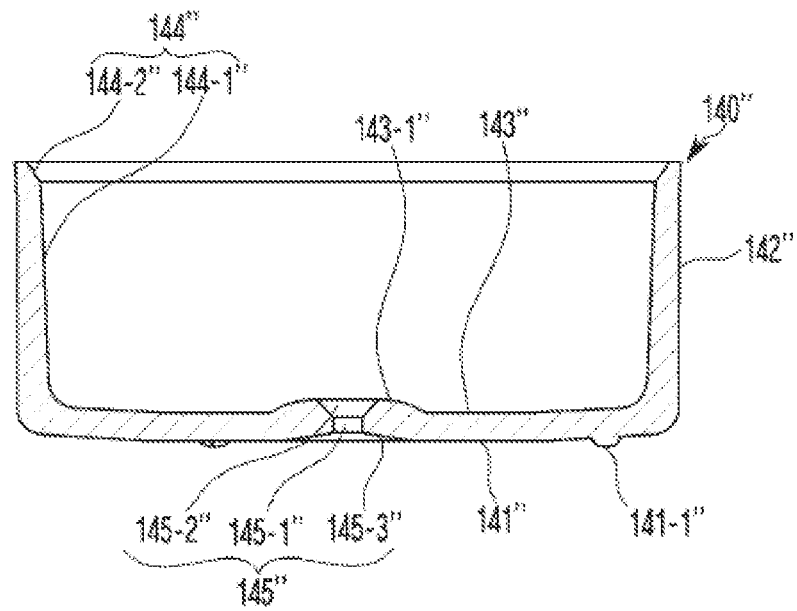
FIG. 8 is a cross-sectional view of the valve body of FIG. 7.
Figure 9:
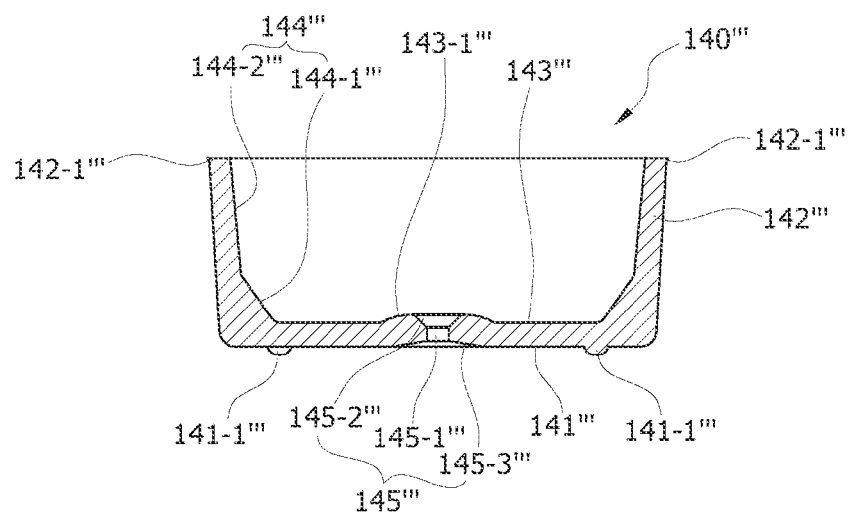
FIG. 9 is a cross-sectional view of a fourth embodiment of the valve body according to the present invention.

FIG. 1 is a perspective view of a container for centrifugation according to an exemplary embodiment of the present invention, FIG. 2 is a perspective view of a cross section A-A of FIG. 1, FIG. 3 is a cross-sectional view of A-A of FIG. 1, FIG. 4 is a perspective view of a first embodiment of a valve body according to the present invention, FIG. 5 is a cross-sectional view of the valve body of FIG. 4, FIG. 6 is a cross-sectional view of a second embodiment of the valve body according to the present invention, FIG. 7 is a perspective view of a third embodiment of the valve body according to the present invention, FIG. 8 is a cross-sectional view of the valve body of FIG. 7, and FIG. 9 is a cross-sectional view of a fourth embodiment of the valve body according to the present invention.

As illustrated in FIGS. 1 to 3, a container 10 for centrifugation according to the present invention is mounted in a centrifuge to separate and collect required components from a complex fluid such as separating red blood cells and the plasma from the blood or separating stem cells from the bone marrow. The container 10 includes a main body including a first chamber 110 in which a material to be centrifuged such as blood or bone marrow is introduced and received and a second chamber 120 in which a suspended material centrifuged from the complex fluid introduced into the first chamber 110 is decanted and received; and a cover 200 which covers the top of the main body 100 and has a fluid communication path P of the decanted suspended material toward the second chamber 120 from the first chamber 110.

The first chamber 110 is formed by a cylinder-shaped outer wall 111 of which an upper portion is opened and a side surface and a bottom surface are closed, and the inside of the first chamber 110 has a valve body 140 which is lifted by a difference in specific gravity from a material to be centrifuged introduced into the first chamber 110 and positioned on the boundary layer between the materials to be centrifuged.

The valve body 140 partitions a deposited material which is moved and positioned to the outside from a rotational center due to relatively large specific gravity when centrifuging the material to be centrifuged and a suspended material which is positioned inside the deposited material relatively close to the rotational center due to relatively small specific gravity to prevent the deposited material from being mixed with the suspended material and discharged in the process of decanting the suspended material toward the second chamber 120. The shape of the valve body 140 has a cup shape in which the upper portion is opened, a minute gap is formed between the outer surface of the valve body 140 and the inner surface of the first chamber 110 so the suspended material may be passed and the valve body 140 may move vertically in the first chamber 110, and through-holes 145 through which the suspended material may pass are formed at the center of the bottom surface of the valve body 140. Accordingly, when the container 10 for centrifugation is mounted on a centrifuge (not illustrated) and rotated, the container 10 for centrifugation is inclined by the centrifugal force and materials having large specific gravity and materials having small specific gravity are separated by the centrifugal force. That is, the deposited materials having large specific gravity are moved to the outer bottom surface 141 side of the valve body 140 through the through-holes 145 formed at the center and the minute gap between the first chamber 110 and the valve body 140, while the suspended materials having small specific gravity are positioned on the inner bottom surface 143 of the valve body 140, so that the deposited materials and the suspended materials may be separated from each other.

The cover 200 is configured by a ring part 230 which forms the rim of the cover 200 and is formed to be coupled to a coupling part 130 at the rim of the cover, a recess part 220 which is connected to the inner side of the ring part 230 to be formed in a recessed shape, and a protrusion part 210 which is connected to the inner side of the recess part 220 and formed in a protruding shape to form the fluid communication path P so that the suspended material is discharged from the first chamber 110 to the second chamber 120. The ring part 230 is coupled to the coupled part 130 of the main body 100 and has a hook-shaped joint to provide easiness of coupling. The configuration of the ring part 230 includes an outer ring part 231 having a ring hook 231-1 formed on an inner peripheral surface, a planar ring part 232 connected to the outer ring part 231, and an inner ring part 233 which is connected with the planar ring part 232 and has a stepped portion, which are sequentially formed to the inside from the outside. The ring hook 231-1 is coupled with a coupling hook 231-1 of the coupling part 130 to be described below, and the assembling is completed by the coupling of the hook. A packing ring 300 is disposed between the inner ring part 233 where the stepped portion is formed and the coupling part 130 to prevent the contents from being leaked from the first chamber 110 and the second chamber 120. As illustrated in FIG. 3, when the cover 200 and the main body 100 are coupled with each other in a state in which the packing ring 300 is placed on the inner side of the coupling part 130 or fitted to the inner ring part 233, the mounting is completed and the contents are prevented from being leaked by the packing ring 300, so that the workability is excellent.

As illustrated in FIG. 3, an inlet port 212 is provided in the protrusion part 210. The inlet port 212 is a port into which a material to be centrifuged such as blood or bone marrow is injected. An inlet packing 212-2 made of silicone or rubber is inserted into the inlet port 212. The inlet packing 212-2 has an insertion hole 212-2 (1) formed at the center and the upper side is clogged to a predetermined thickness. Accordingly, after the material to be centrifuged such as blood or bone marrow is injected into the first chamber 110 through the inlet port 212 using an injection needle (not illustrated), the contents are not discharged even when removing the injection needle. In addition, an injection needle guide 212-1 having a hole 212-1 (1) formed at the center is mounted on the upper portion of the inlet port 212 so as to insert the injection needle correctly. Accordingly, a user may easily insert the injection needle into the first chamber 110 using the injection needle guide 212-1 and may easily inject the material to be centrifuged such as blood or bone marrow through the injection needle.

As illustrated in FIG. 3, a discharge port 222 is formed in the recess part 220. The discharge port 222 also has the same structure as the inlet port 212 and serves to discharge the suspended material such as PPP or PRP decanted into the second chamber 120. The discharge port 222 is also inserted with a discharge packing 222-2 made of silicone or rubber like the inlet port 212. The discharge packing 222-2 has an insertion hole 222-2 (1) formed at the center and the upper side is clogged to a predetermined thickness. Accordingly, after the PPP or PRP decanted through the discharge port 222 using the injection needle (not illustrated) is injected to the injection needle, even when removing the injection needle, the contents are not discharged. In addition, an injection needle guide 222-1 having a hole 222-1 (1) formed at the center is mounted on the upper portion of the discharge port 222 so as to insert the injection needle correctly. Accordingly, a user may easily insert the injection needle into the second chamber 120 using the injection needle guide 222-1 and may discharge the centrifuged PPP or PRP from the second chamber 120 through the injection needle.

In addition, an air vent 224 is provided in the recess part 220. The air vent 224 is finely provided so that the contents are not discharged but the air may be discharged. The air vent 224 is configured to allow the air in the main body 100 to be discharged when the material to be centrifuged is injected into the first chamber 110. It is preferable that the air vent 224 is formed on the upper portion of the second chamber 120 because the recess part 220 excluding the upper portion of the second chamber 120 is in contact with the coupling part 130.

As illustrated in FIGS. 1 to 3, the second chamber 120 is spaced apart from the outside of the first chamber 110 to cover a part of the outer wall 111 of the first chamber 110 and includes an inner wall 122 and an outer wall 121 having a concentric structure with the outer wall 111 of the first chamber 110. The upper end of the inner wall 122 of the second chamber 120 is connected to the upper end of the first chamber 110 by a connection part 112. The second chamber 120 has a shape in which the cross-sectional area gradually decreases from the upper end to the lower end, and the lower portion of the second chamber 120 is configured by a first bottom part 123 which is the lowest bottom having an inclined shape to easily extract the suspended material received in the second chamber 120 and a second bottom part 124 formed to be inclined at the upper portion of the first bottom part 123, so that the cross-sectional area gradually decreases toward the lower portion.

As illustrated in FIGS. 2 and 3, a spaced space between the connection part 112 at the upper end of the outer wall 111 of the first chamber 110 and the protrusion part 220 of the cover 200 forms the fluid communication path P between the first chamber 110 and the second chamber 120, and the suspended material by the centrifugation moves to the second chamber 120 through the path P.

FIGS. 4 to 5 are views of a first embodiment of the valve body 140. As illustrated in FIGS. 4 and 5, the valve body 140 is configured by an inner bottom surface 143, an outer bottom surface 141 forming a lower surface of the inner bottom surface 143, an inner surface 144 connected with the inner bottom surface 143, an outer surface 142 forming the outer portion of the inner surface 144 and connected with the outer bottom surface 141, and a through-hole 145 formed by passing through the inner bottom surface 143 and the outer bottom surface 141 to be formed in a cup shape as a whole. A foot plate 141-1 protrudes from the outer bottom surface 141 to provide a gap between the valve body 140 and the bottom surface of the first chamber 110, and a sufficient gap is formed during centrifugation so that the deposited material may be easily injected, thereby being able to be rapidly centrifuged. In addition, for smooth decanting by centrifugation, in the inner surface 144, a first slope surface 144-1 and a second slope surface 144-2 are formed sequentially from the lower portion to the upper portion for smooth movement of the suspended material. Thus, the centrifuged suspended material may be easily decanted from the first chamber 110 to the second chamber 120. A through-hole 145 is formed at the center, and the through-hole 145 is configured by a straight pipe part 145-1 formed upward from the outer bottom surface 141 and an enlarged pipe part 145-2 of which a diameter is enlarged to the upper portion from the end portion of the straight pipe part 145-1. Further, in order to extend the enlarged pipe part 145-2 and 145-2', the inner bottom surfaces 143 and 143' are further provided with hill parts 143-1 and 143-1' protruding from the center thereof. According to the above-described configuration, the deposited material may be easily discharged by the enlarged pipe part 145-2', and it is difficult to flow back the deposited material through the straight pipe part 145-1', so that the centrifugation can be performed quickly and accurately.

A second embodiment of FIG. 6 has the same configuration as the embodiment of FIG. 4, but has a difference in that an outer surface 142' is inclined outward so as to have a larger diameter upward and an outer surface minute protrusion part 142-1' is further formed on an upper end of the outer surface 142'. Particularly, a valve body 140' is configured by an inner bottom surface 143', an outer bottom surface 141' forming a lower surface of the inner bottom surface 143', an inner surface 144' connected with the inner bottom surface 143', an outer surface 142' forming the outer portion of the inner surface 144' and connected with the outer bottom surface 141', and a through-hole 145' formed by passing through the inner bottom surface 143' and the outer bottom surface 141' to be formed in a cup shape as a whole. A foot plate 141-1' protrudes from the outer bottom surface 141', the inner surface 144' has a first slope surface 144-1' and a second slope surface 144-2' formed sequentially from the lower portion to the upper portion for smooth movement of the suspended material. The outer surface has a larger diameter upward and is formed so as to be inclined toward the upper side when viewed in section, and the upper end of the outer surface 142' has an outer surface minute protrusion part 142-1' minutely protruding outward along the outer surface. In the present embodiment, there is an advantage that a contact area between the valve body 140' and the inner wall of the first chamber is reduced, and smooth movement due to buoyancy of the valve body 140' is possible. A through-hole 145' is formed at the center, and the through-hole 145' is configured by a straight pipe part 145-1' formed upward from the outer bottom surface 141' and an enlarged pipe part 145-2' of which a diameter is enlarged to the upper portion from the end portion of the straight pipe part 145-1'. In order to extend the enlarged pipe part 145-2', the inner bottom surface 143' is further provided with a hill part 143-1 and 143-1' protruding from the center thereof. The structure of the second embodiment is the same as that of the first embodiment except for the outer surface protrusion part 142-1', so the detailed description will be omitted.

FIGS. 7 and 8 illustrate a third embodiment of a valve body 140". As illustrated in FIGS. 7 and 8, the valve body 140" is configured by an inner bottom surface 143", an outer bottom surface 141" forming a lower surface of the inner bottom surface 143", an inner surface 144" connected with the inner bottom surface 143", an outer surface 142" forming the outer portion of the inner surface 144" and connected with the outer bottom surface 141", and a through-hole 145" formed by passing through the inner bottom surface 143" and the outer bottom surface 141" to be formed in a cup shape as a whole. A foot plate 141-1" is formed to protrude from the outer bottom surface 141", a predetermined gap is formed between the bottom surface of the first chamber 110 and the valve body 140" by the foot plate 141-1" so that the deposited material may be first deposited in the space, thereby performing the centrifugation rapidly and accurately. The inner surface 144" forms a gentle slope surface 144-1" at a predetermined angle from the bottom to the top for smooth movement of the suspended material, and the end portion of the inner surface has a cutting surface 144-2" cut along the inner peripheral surface to reduce the load. Further, a through-hole 145" is formed at the center, and the through-hole 145" is configured by an undercut part 145-3" cutting a part of the lower portion of a straight pipe part 145-1" formed for smooth flow of the suspended material upward from the outer bottom surface 141", the straight pipe part 145-1" formed on the upper portion of the undercut part 145-3", and an enlarged pipe part 145-2" of which a diameter is enlarged to the upper portion from the end portion of the straight pipe part 145-1". A hill part 143-1" is formed to protrude from the center of the inner bottom surface 143" to extend the enlarged pipe part 145-2". According to the above-described configuration, the deposited material may be easily discharged by the enlarged pipe part 145-2", and it is difficult to flow back the deposited material through the straight pipe part 145-1", so that the centrifugation can be performed quickly and accurately. Further, the suspended material below the valve body 140" may be easily discharged through the undercut part 145-3" below the straight pipe part 145-1".

FIG. 9 illustrates a fourth embodiment of a valve body 140'''. As illustrated in FIG. 9, the fourth embodiment has the same configuration as the third embodiment except that the outer surface increases in diameter toward the upper portion and an outer surface minute protrusion part 142-1''' is included. An outer diameter increases toward the upper portion and the outer surface minute protrusion part 142-1''' is configured to reduce the contact area where the valve body 140''' and the inner wall of the first chamber 110 are in contact with each other. Particularly, the valve body 140''' is configured by an inner bottom surface 143''', an outer bottom surface 141''' forming a lower surface of the inner bottom surface 143''', an inner surface 144''' connected with the inner bottom surface 143''', an outer surface 142''' forming the outer portion of the inner surface 144''' and connected with the outer bottom surface 141''', and a through-hole 145''' formed by passing through the inner bottom surface 143''' and the outer bottom surface 141''' to be formed in a cup shape as a whole. A foot plate 141-1''' is formed to protrude from the outer bottom surface 141''', and the inner surface 144''' forms a slope surface 144-1''' at a predetermined angle to the upper portion from the lower portion for smooth movement of the suspended material. and the end portion of the inner surface has a cutting surface 144-2''' cut along the inner peripheral surface to reduce the load. The outer surface 142''' has a larger diameter toward the upper portion so that the cross section has a shape inclined outward, and the upper end of the outer surface 142''' has an outer surface minute protrusion part 142-1''' protruding outward along the outer peripheral surface. Further, a through-hole 145''' is formed at the center, and the through-hole 145''' is configured by an undercut part 145-3''' cutting a part of the lower portion of a straight pipe part 145-1''' formed for smooth flow of the suspended material upward from the outer bottom surface 141''', the straight pipe part 145-1''' formed on the upper portion of the undercut part 145-3''', and an enlarged pipe part 145-2''' of which a diameter is enlarged to the upper portion from the end portion of the straight pipe part 145-1'''. A hill part 143-1''' is formed to protrude from the center of the inner bottom surface 143''' to extend the enlarged pipe part 145-2'''. According to the above-described configuration, the deposited material may be easily discharged by the enlarged pipe part 145-2''', and it is difficult to flow back the deposited material through the straight pipe part 145-1''', so that the centrifugation can be performed quickly and accurately. Further, the suspended material below the valve body 140''' may be easily discharged through the undercut part 145-3''' below the straight pipe part 145-1".

In this specification, the configurations and the functions of the container 10 for centrifugation have been described by describing the centrifuging and decanting process of the blood 300 as an example. However, the container 10 for centrifugation of the present invention is not limited to these embodiments and may be applied to a case of centrifuging and collecting other various complex fluids such as bone marrow for each component.

The present invention relates to a container for centrifugation by applying a centrifugal force to a biological complex fluid such as blood or bone marrow by a difference in specific gravity for each component and there is industrial availability because the container for centrifugation can be mass-produced and applicable to the medical industry.

The invention claimed is:

1. A container for centrifugation comprising:
a main body (100) including a first chamber (110) in which a material to be centrifuged is received, a second chamber (120) in which a suspended material centrifuged from the material in the first chamber (110) is decanted from the first chamber (110) and received and which is positioned on one side of the first chamber (110), and a coupling part (130) formed to surround the first chamber (110) and the outside of the upper end of the second chamber (120); and
a cover (200) which covers an upper portion of the main body (100) and forms a fluid communication path (P) of the decanted suspended material between the first chamber (110) and the second chamber (120),
wherein the inside of the first chamber (110) has a valve body (140') which is disposed to linearly reciprocate in a longitudinal direction of the first chamber (110) to be positioned on a boundary layer between the centrifuged materials and have a through-hole (145') formed on the bottom surface and through which the material to be centrifuged is separately moved,
the cover (200) is configured by a ring part (230) which forms the rim of the cover (200) and is formed to be coupled to the coupling part (130) at the rim of the cover, a recess part (220) which is connected to the inner side of the ring part (230) to be formed in a recessed shape, and a protrusion part (210) which is connected to the inner side of the recess part (220) and formed in a protruding shape to form the fluid communication path (P) so that the suspended material is discharged from the first chamber (110) to the second chamber (120),
in the protrusion part (210), an inlet port (212) is formed to protrude from the protrusion part (210) for injecting the material to be centrifuged to the first chamber (110),
the recess part (220) has an air vent for discharging inner air by injecting the material to be centrifuged to the first chamber (110) and a discharge port for discharging a suspended material introduced into the second chamber (120),
the ring part (230) includes an outer ring part (231), a planar ring part (232) connected to the outer ring part (231), and an inner ring part (233) which is connected with the planar ring part (232) and has a stepped portion, wherein a ring hook (231-1) is formed on an inner peripheral surface of the outer ring part (231), and
an outer end portion of the coupling part (130) has a coupling hook (131) which is extended upward and corresponds to an outer peripheral surface so as to be coupled with the ring hook (231-1) of the outer ring part (231),
wherein the valve body (140') is configured by an inner bottom surface (143'), an outer bottom surface (141') forming a lower surface of the inner bottom surface (143'), an inner surface (144') connected with the inner bottom surface (143'), an outer surface (142') forming the outer portion of the inner surface (144') and connected with the outer bottom surface (141'), and the through-hole (145') formed by passing through the inner bottom surface (143') and the outer bottom surface (141') to be formed in a cup shape as a whole, and a foot plate (141-1') protrudes from the outer bottom surface (141'), the inner surface (144') has a first slope surface (144-1') and a second slope surface (144-2') formed sequentially from the lower portion to the upper portion for smooth movement of the suspended material, the outer surface (142') has a larger diameter upward and is formed so as to be inclined upward, and the upper end of the outer surface (142') has an outer surface minute protrusion part (142-1') minutely protruding outward along the outer peripheral surface.

2. The container for centrifugation of claim 1, wherein the through-hole (145') is configured by a straight pipe part (145-1') formed upward from the outer bottom surface (141') and an enlarged pipe part (145-2') having a diameter enlarged to an upper portion from an end portion of the straight pipe part (145-1'), and in order to extend the enlarged pipe part (145-2'), the inner bottom surface (143') is provided with a hill part (143-1') protruding from a center thereof.

3. A container for centrifugation comprising:

a main body (100) including a first chamber (110) in which a material to be centrifuged is received, a second chamber (120) in which a suspended material centrifuged from the material in the first chamber (110) is decanted from the first chamber (110) and received and which is positioned on one side of the first chamber (110), and a coupling part (130) formed to surround the first chamber (110) and the outside of the upper end of the second chamber (120); and a cover (200) which covers an upper portion of the main body (100) and forms a fluid communication path (P) of the decanted suspended material between the first chamber (110) and the second chamber (120), wherein the inside of the first chamber (110) has a valve body (140''') which is disposed to linearly reciprocate in a longitudinal direction of the first chamber (110) to be positioned on a boundary layer between the centrifuged materials and have a through-hole (145''') formed on the bottom surface and through which the material to be centrifuged is separately moved, the cover (200) is configured by a ring part (230) which forms the rim of the cover (200) and is formed to be coupled to the coupling part (130) at the rim of the cover, a recess part (220) which is connected to the inner side of the ring part (230) to be formed in a recessed shape, and a protrusion part (210) which is connected to the inner side of the recess part (220) and formed in a protruding shape to form the fluid communication path (P) so that the suspended material is discharged from the first chamber (110) to the second chamber (120), in the protrusion part (210), an inlet port (212) is formed to protrude from the protrusion part (210) for injecting the material to be centrifuged to the first chamber (110), the recess part (220) has an air vent for discharging inner air by injecting the material to be centrifuged to the first chamber (110) and a discharge port for discharging a suspended material introduced into the second chamber (120), the ring part (230) includes an outer ring part (231), a planar ring part (232) connected to the outer ring part (231), and an inner ring part (233) which is connected with the planar ring part (232) and has a stepped portion, wherein a ring hook (231-1) is formed on an inner peripheral surface of the outer ring part (231), and an outer end portion of the coupling part (130) has a coupling hook (131) which is extended upward and corresponds to an outer peripheral surface so as to be coupled with the ring hook (231-1) of the outer ring part (231), wherein the valve body (140''') is configured by an inner bottom surface (143'''), an outer bottom surface (141''') forming a lower surface of the inner bottom surface (143'''), an inner surface (144''') connected with the inner bottom surface (143'''), an outer surface (142''') forming the outer portion of the inner surface (144''') and connected with the outer bottom surface (141'''), and a through-hole (145''') formed by passing through the inner bottom surface (143''') and the outer bottom surface (141''') to be formed in a cup shape as a whole, and a foot plate (141-1''') is formed to protrude from the outer bottom surface (141'''), the inner surface (144''') forms a slope surface (144-1''') at a predetermined angle to the upper portion from the lower portion for smooth movement of the suspended material, the outer surface (142''') has a larger diameter toward the upper portion so that the cross section has a shape inclined outward, and the upper end of the outer surface (142''') has an outer surface minute protrusion part (142-1''') protruding outward along the outer peripheral surface.

4. The container for centrifugation of claim 3, wherein the through-hole (145''') is configured by an undercut part (145-3') formed for smooth flow of the suspended material upward from the outer bottom surface (141'''), a straight pipe part (145-1''') formed on an upper portion of the undercut part (145-3"), and an enlarged pipe part (145-2''') having a diameter enlarged to an upper portion from an end portion of the straight pipe part (145-1'''), and in order to extend the enlarged pipe part (145-2'''), the inner bottom surface (143''') is provided with a hill part (143-1') protruding from a center thereof.

* * * * *